(12) United States Patent
Hantash

(10) Patent No.: US 8,647,871 B2
(45) Date of Patent: Feb. 11, 2014

(54) ENDOGENOUS EXPRESSION OF HLA-G AND/OR HLA-E BY MESENCHYMAL CELLS

(75) Inventor: Basil M. Hantash, East Palo Alto, CA (US)

(73) Assignee: Escape Therapeutics, Inc., San Jose, CA (US)

( * ) Notice: Subject to any disclaimer, the term of this patent is extended or adjusted under 35 U.S.C. 154(b) by 123 days.

(21) Appl. No.: 12/532,512

(22) PCT Filed: Mar. 28, 2008

(86) PCT No.: PCT/US2008/058779
§ 371 (c)(1),
(2), (4) Date: Sep. 22, 2009

(87) PCT Pub. No.: WO2008/121894
PCT Pub. Date: Oct. 9, 2008

(65) Prior Publication Data
US 2010/0055785 A1    Mar. 4, 2010

Related U.S. Application Data

(60) Provisional application No. 60/920,989, filed on Mar. 30, 2007.

(51) Int. Cl.
*C12N 5/00* (2006.01)
*C12N 5/071* (2010.01)
*C12N 5/02* (2006.01)

(52) U.S. Cl.
USPC .......................... 435/366; 435/325; 435/372

(58) Field of Classification Search
USPC ......................................... 435/325, 366, 372
See application file for complete search history.

(56) References Cited

U.S. PATENT DOCUMENTS 7,410,773 B2 *  8/2008  Abuljadayel ................. 435/7.8
2005/0287603 A1 * 12/2005  Gorczynski ................... 435/7.2

FOREIGN PATENT DOCUMENTS

WO    WO 2006/111706 A    10/2006

OTHER PUBLICATIONS

Gronthos et al., 2001, J Cellular Physiology, vol. 189, pp. 54-63.*
Yelavarthi et al., 1991, J. Immunology, vol. 146(8), pp. 2847-2854.*
Meisel et al., 2005, Blood, vol. 103(12), pp. 4619-4621.*
Romanov et al., 2005, Cell Technologies in Biology and Medicine, No. 3, pp. 138-143.*
Kawabata et al., 2005, Molecular Pharmaceutics, vol. 3(2), pp. 95-103.*
Abstracts from the 4th International Conference of HLA-G, 2006, Tissue Antigens, vol. 68, pp. 349-368.*
Nasef et al. (2004, Blood, ASH Annual Meeting Abstracts, vol. 104, Abstract 4251). 1 page printout.*
Götherström, Cecilia, et al., "Difference in Gene Expression Between Human Fetal Liver and Adult Bone Marrow Mesenchymal Stem Cells," Haematologica/The Hematology Journal, 2005; 90(8), 1017-1026.
Int'l Search Report from PCT/US2008/058779, mailed Mar. 10, 2009.
Aisha Nasef et al., "Immunosupressive Effects of Mesenchymal Stem Cells: Involvement of HLA-G", Transplantation, vol. 84, No. 2, Jul. 27, 2007, pp. 231-237.
Le Blanc Katarina et al., "HLA Expression and Immunologic Properties of Differentiated and Undifferentiated Mesenchymal Stem Cells," Experimental Hematology, NY, NY, US, vol. 31, No. 10, Oct. 1, 2003, pp. 890-896.
Apps, R. et al. "A critical look at HLA-G," Trends in Immunology, vol. 29, No. 7, pp. 313-321 (2008).
Nasef, A. et al. "Immunisuppressive Effects of Mesenchymal Stem Cells: Involvement of HLA-G," Transplantation, vol. 84, No. 2, pp. 231-237, Jul. 27, 2007.
Rajagopalan, S. et al. "Activation of NK Cells by an Endocytosed Receptor for Soluble HLA-G," PLoS Biology, Jan. 2006, vol. 4, Issue 1, e9, pp. 0070-0086.
Dicker, Andrea et al. "Functional Studies of Mesenchymal Stem Cells Derived from Adult Human Adipose Tissue." Experimental Cell Research, vol. 308., No. 2, Aug. 15, 2005. 9 pages.
Dominici, M. et al. "Minimal Criteria for Defining Multipotent Mesenchymal Stromal Cells. The International Soceity for Cellular Therapy Position Statement." Cytotherapy, vol. 8, No. 4. 2006. 3 pages.
Lee, Ryang Hwa et al. "Characterization and Expression Analysis of Mesenchymal Stem Cells from Human Bone Marrow and Adipose Tissue." Cellular Physiology and Biochemistry. vol. 14. Apr. 15, 2004, 14 pages.
Oedayrajsingh-Varma, MJ et al. "Adipose Tissue-Derived Mesenchymal Stem Cell Yield and Growth Characteristics are Affected by the Tissue-Harvesting Procedure." Cytotherapy. vol. 8, No. 2. 2006. 12 pages.
Schaffler, Andreas et al. "Concise Review: Adipose Tissue-Derived Stromal Cells—Basic and Clinical Implications for Novel Cell-based Therapies." Stem Cells. vol. 25. Dec. 1, 2006. 10 pages.
Sengenes, Coralie et al. "Preadipocytes in the Human Subcutaneous Adipose Tissue Display Distinct Features from the Adult Mesenchymal and Hemtopoietic Stem Cells." Journal of Cellular Physiology, vol. 205, No. 1, Oct. 2005. 10 pages.
Wagner, Wolfgang et al. "Comparative Characteristics of Mesenchymal Stem Cells from Human Bone Marrow, Adipose Tissue, and Umbilical Cord Blood." Experimental Hematology, vol. 33. Jul. 11, 2005. 15 pages.

* cited by examiner

Primary Examiner — Anoop Singh
Assistant Examiner — David A Montanari
(74) Attorney, Agent, or Firm — Wilmer Cutler Pickering Hale and Dorr LLP

(57) ABSTRACT

Methods and compositions are provided for the identification and isolation of mammalian HLA-G+ MSC, HLA-E+ MSC, or HLA-G4VHLA-E+ MSC. The methods of the invention provide a means to obtain enriched HLA-G+ MSC, HLA-E+ MSC, or HLA-G+/HLA-E+ MSC populations.

7 Claims, 12 Drawing Sheets

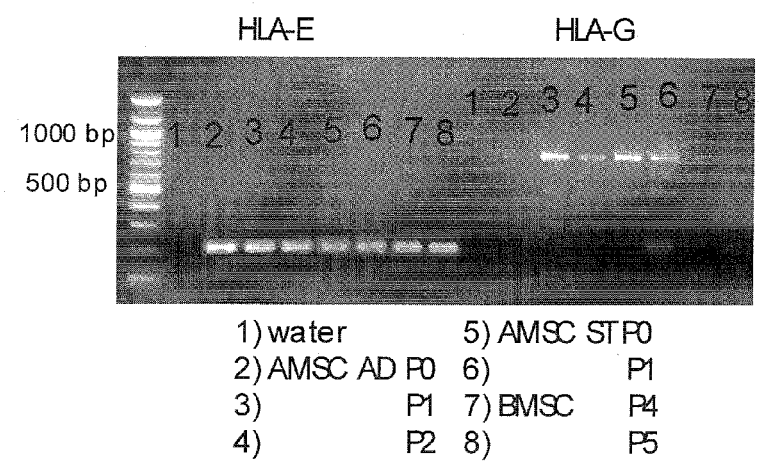
FIGURE 6A
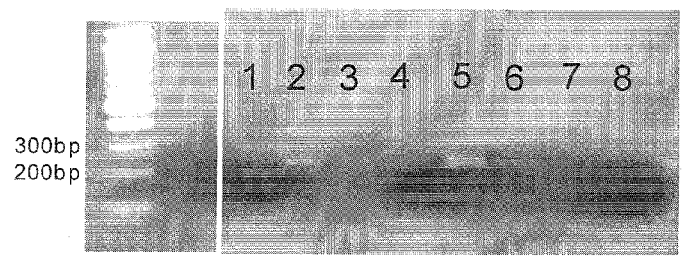
FIGURE 6B
FIGURE 6C
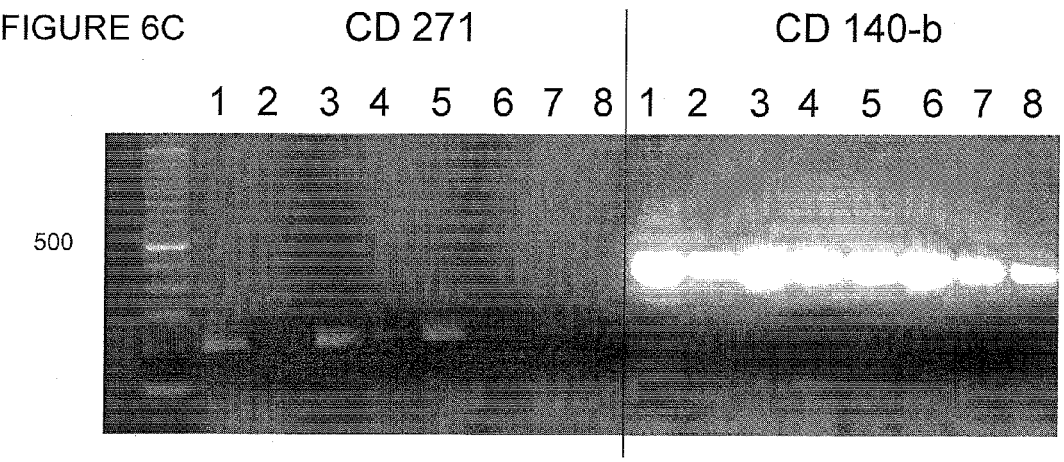

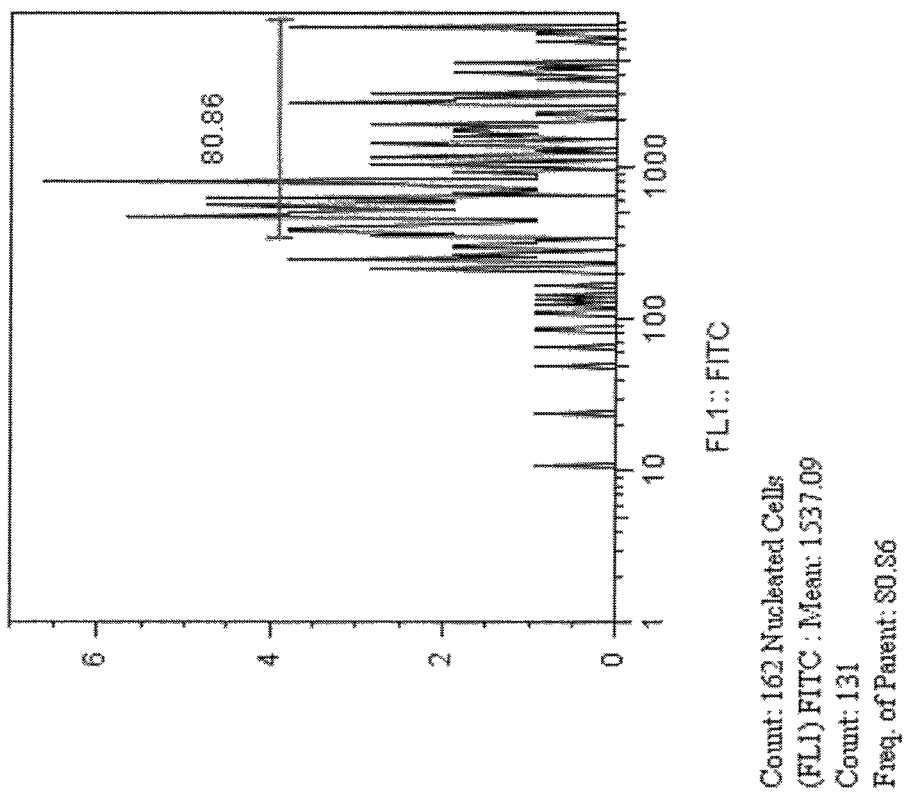

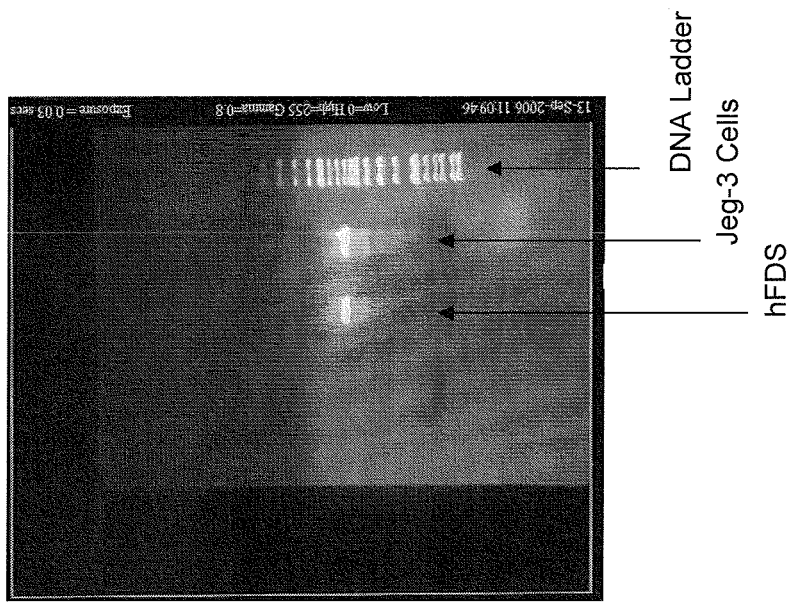
FIGURE 8. HLA-G positive MSCs. Positive control Jeg-3 cells.

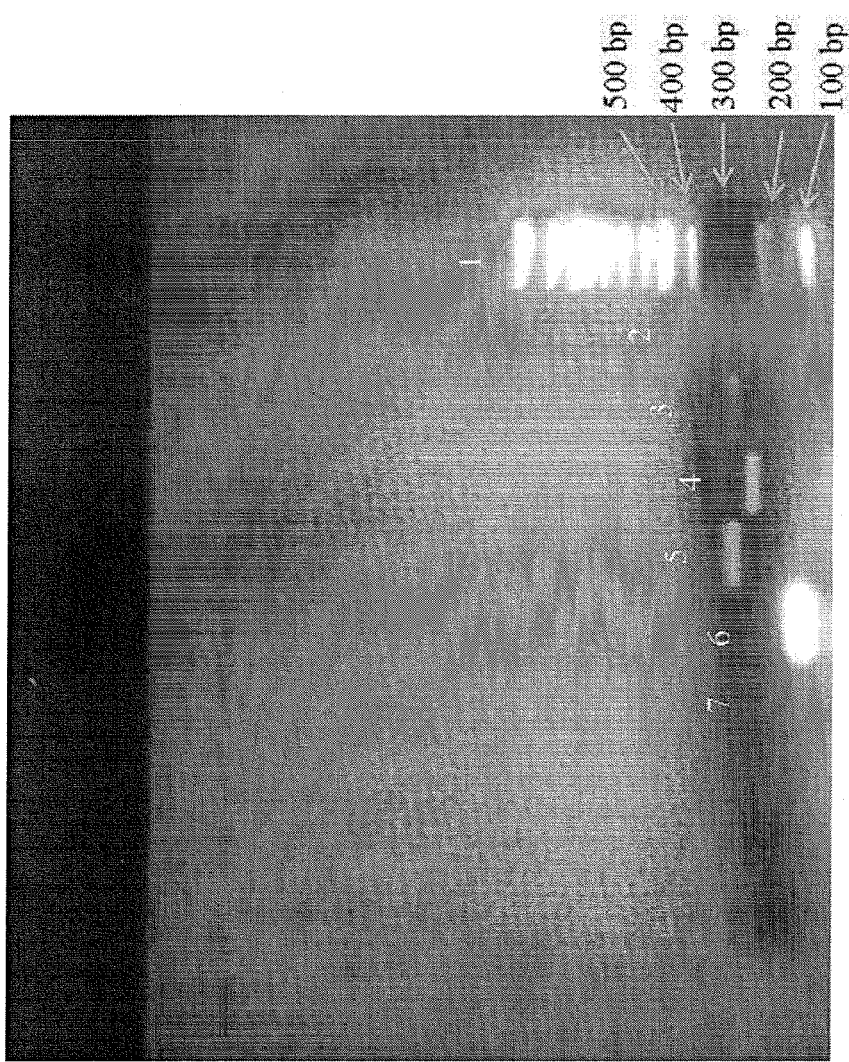
FIGURE 9. Profile of HLA-G negative MSCs.
Legend from right to left:
1. Ladder 2. Null sample 3. Beta-Actin 4. HLA-A 5. HLA-B 6. HLA-C 7. HLA-G

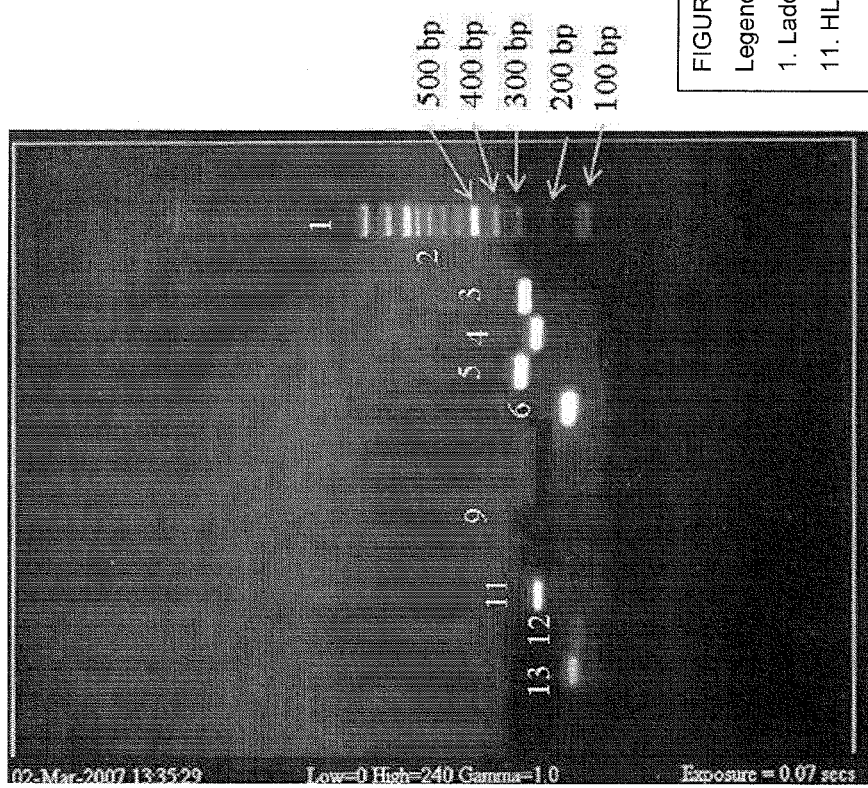
FIGURE 10. HLA-G (-) MSCs.
Legend from right to left:
1. Ladder  2. Null sample  3. Beta-Actin  4. HLA-A  5. HLA-B  6. HLA-C  9. HLA-G
11. HLA-DP  12. HLA-DQ  13. HLA-DR

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcggctacta caaccagagc                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaggtaggc tctcaactgc                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gacacccagt tcgtgaggtt                                                   20

<210> SEQ ID NO 4
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
gatgtaatcc ttgccgtcgt                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggctacta caaccagagc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatgtaatcc ttgccgtcgt                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaccttccag atcctggtga                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctttcttgct cctcctgtgc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagatcaaag tccggtggtt                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 10
tcaccaggat ctggaaggtc                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagttcctcg gagtggagag                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcagcatct tgctctgtgc                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atttccacac ttccgtgtcc                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcaggttcac tcggaaaatc                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccaccaccct gtctttgact                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 16
tggcacgtgt atctctgctc                                           20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagtactccg tgtggatcgg                                           20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caccttcacc gttccagttt                                           20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
taacctcctt cgtcattgcc                                           20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctccaaatc ggagtccatc                                           20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tacctacagc ctggtttggg                                           20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
tggttgagtt ttggagtccc                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcgctgttgg aaatagcttc                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caggacgtca aagcactgaa                                               20
```

ENDOGENOUS EXPRESSION OF HLA-G AND/OR HLA-E BY MESENCHYMAL CELLS

CROSS-REFERENCE TO RELATED APPLICATIONS

This application claims priority from 35 U.S.C. §119(e) to U.S. Provisional Patent Application No. 60/920,989, filed Mar. 30, 2007, which is hereby incorporated by reference in its entirety.

BACKGROUND INFORMATION

Autoimmune diseases and transplantation related problems remain major public health problems worldwide. Although immunosuppressive drugs are in wide use and have shown effectiveness, their clinical usefulness has been limited due to their toxicity and other short- and long-term side effects such as risk of malignancy. Currently there is a need for new immunomodulatory agents with improved immunosuppressant activity and pharmacokinetic properties, improved bioavailability, greater potency, extended effective half-life in vivo, fewer side effects and less complicated dosing schedules.

Key to immune function and transplantation rejection are the major histocompatibility antigens, commonly referred to in humans as the HLA complex. Genes encoding class I HLA proteins are clustered at the telomeric end of human chromosome 6p21. These include the classical class Ia proteins, HLA-A, -B and -C, which are ubiquitously expressed, and are highly polymorphic. In contrast, the non-classical class Ib proteins, HLA-E, HLA-F and HLA-G, are relatively invariant, and are selectively expressed.

HLA-G is an antigen of great interest, and the focus of significant experimental evaluation. Features important to the function of this molecule include a low number of functionally different alleles; seven alternatively spliced transcripts, four encoding membrane-bound proteins and three encoding soluble proteins; and the generation of proteins with a truncated cytoplasmic tail, revealing a cryptic retrieval motif that may interfere with presentation of exogenous peptides.

In HLA-G, nine polymorphisms have been identified in the exons encoding the extracellular domain, and one in the 3' untranslated region. Of the nine, five result in amino acid differences and four do not. One major deletion has been identified: a single base pair (bp) deletion at nucleotide 1597, which causes a frameshift at amino acid 130. This deletion of a cytosine residue at codon 130 results in a null allele (called G*0105N), which does not encode functional HLA-G1 or HLA-G5 protein isoforms.

The full-length isoform, HLA-G1, is structurally similar to other class I genes, except for the truncated cytoplasmic tail. The G2 isoform results from the removal of exon 3; the resulting heavy chain cannot form heterodimers with β2 microglobulin and homodimerizes to form an HLA class-II-like structure. HLA-G1 and HLA-G2 are also expressed as soluble proteins (called HLA-G5 and HLA-G6, respectively) because of the inclusion of intron 4 sequences in the mature mRNA. HLA-G5 and HLA-G6 secreted proteins include a unique sequence of 21 amino acids. HLA-G5 may or may not associate with β2m, whereas HLA-G6 does not. HLA-G3 results from the removal of exons 3 and 4. HLA-G4 and HLA-G7 mRNAs are scarce in placentas, and the functions of their protein products remain unknown. The soluble HLA-G isoforms circulate in mothers' blood throughout pregnancy. Soluble HLA-G is also produced by some but not by all preimplantation embryos.

HLA-G is involved in the induction of immune tolerance. Its effects include impact on NK cell killing, migration, and cell viability; proliferation and IFNγ production; regulation of cytokine production in blood mononuclear cells and cytotoxic T lymphocytes (CTLs); suppression of CTL killing and viability; inhibition of proliferation and induction of a suppressive phenotype in T-helper cells; and alteration of dendritic cell stimulatory capacity and maturation of this lineage.

The major receptors for HLA-G on leukocytes are the leukocyte-inhibitory receptors (LILRB), formerly known as the immunoglobulin-like transcript (ILT) receptors. LILRBs are expressed by T and B lymphocytes and also by NK cells and mononuclear phagocytes, and LILRBs abrogate activating signals received by these cells. Although LILRB1 (ILT2) appears to be the main binding protein for lymphocytes, LILRB2 (ILT4) may be the main receptor for HLA-G, which is exhibited by monocyte/macrophages, the second most populous leukocyte population in the human decidua.

Similar to HLA-G, cell surface expression of HLA-E is limited, although it is transcribed in all human tissue. The limited number of peptides capable of binding to HLA-E include nonamer peptides derived from the signal sequence of classical MHC or of HLA-G molecules and stress-associated autologous and pathogen molecules. When bound to signal peptides from classical MHC class I molecules, HLA-G or CMV, HLA-E triggers the inhibitory NK receptor, CD94/NKG2A.

Since most NK cells and T cells express CD94/NKG2A, it is hypothesized that expression of HLA-E inhibits the activities of CD94/NKG2A-expressing effector cells. Indeed, induction of HLA-E expression by target cells led to a significant inhibition of both lysis and cytokine secretion by CD94/NKG2A-expressing NK cells or CTL (see, e.g., Borrego et al. (1998) *J. Exp. Med.* 187: 813-818; Braud et al (2003) *Trends Immunol.* 24: 162-164; Le Drean et al. (1998) *Eur. J. Immunol.* 28: 264-276).

The therapeutic implication of cells expressing HLA-G and/or HLA-E is tremendous. Identification of long-lived stem cell populations that express these proteins are of interest for various clinical and research purposes. The present invention addresses this need.

SUMMARY OF EXEMPLARY EMBODIMENTS

Compositions and methods are provided that relate to the isolation, identification and use of human mesenchymal stem cells expressing endogenous HLA-G (HLA-G$^+$ MSC), HLA-E$^+$ (HLA-E$^+$ MSC), or HLA-G and HLA-E (HLA-G$^+$/HLA-E$^+$ MSC); wherein such expression may be intracellular, as a cell surface marker(s), and/or as soluble protein. Uses of these cells include the induction and maintenance of immune system regulation in post-infectious, inflammatory, allergic, autoimmune, allo-immune, vasculitic, degenerative vascular, and graft versus host diseases. The cells are present as a minor population in mesenchymal stem cells isolated, for example, from adult human adipose tissue.

The cells of the invention find use in therapeutic methods, e.g. as immunomodulatory agents, e.g. for co-transplantation with a source of hematopoietic stem cells, with solid tissue transplantation; and the like. In one embodiment of the invention, the HLA-G expressing MSC provide an immunomodulatory medicament for inhibiting the activity of killer cells, in particular NK cells. In another embodiment, the HLA-G expressing MSC provide an immunomodulatory medicament for inhibiting graft rejection.

In another embodiment of the invention, an exogenous nucleic acid is introduced into a population of cells comprising MSC selected from the group consisting of HLA-G+ MSC, HLA-E+ MSC, and HLA-G+/HLA-E+ MSC. The exogenous nucleic acid comprises at least one sequence encoding a protein product of interest. In a preferred embodiment, the nucleic acid encodes for HLA-G. Such cells may find use in transplantation, gene therapy and the like, where overexpression of HLA-G protects the cell from host immune responses.

BRIEF DESCRIPTION OF THE FIGURES

FIG. 6A-6C are gels of RT-PCR amplification products of from human adipose mesenchymal stem cells (AMSC) from two patients (AD or ST) that were freshly isolated (P0) once (P1), twice (P2), thrice (P3), four times (P4) or bone marrow stem cells (BMSC) passage four times (P4), five times (P5), six times (P6), seven times (P7) using primers specific for HLA-E or HLA-G (FIG. 6A) idoleamine-pyrrole 2,3 dioxygenase (INDO; FIG. 6B), CD271 or CD140b (FIG. 6C) in the absence or presence of Interferon-γ (IFN-γ).

FIG. 8. HLA-G positive MSCs.

FIG. 9. Profile of HLA-G negative MSCs.

FIG. 10. HLA-G (−) MSCs.

DETAILED DESCRIPTION OF EXEMPLARY EMBODIMENTS

Figure 1:
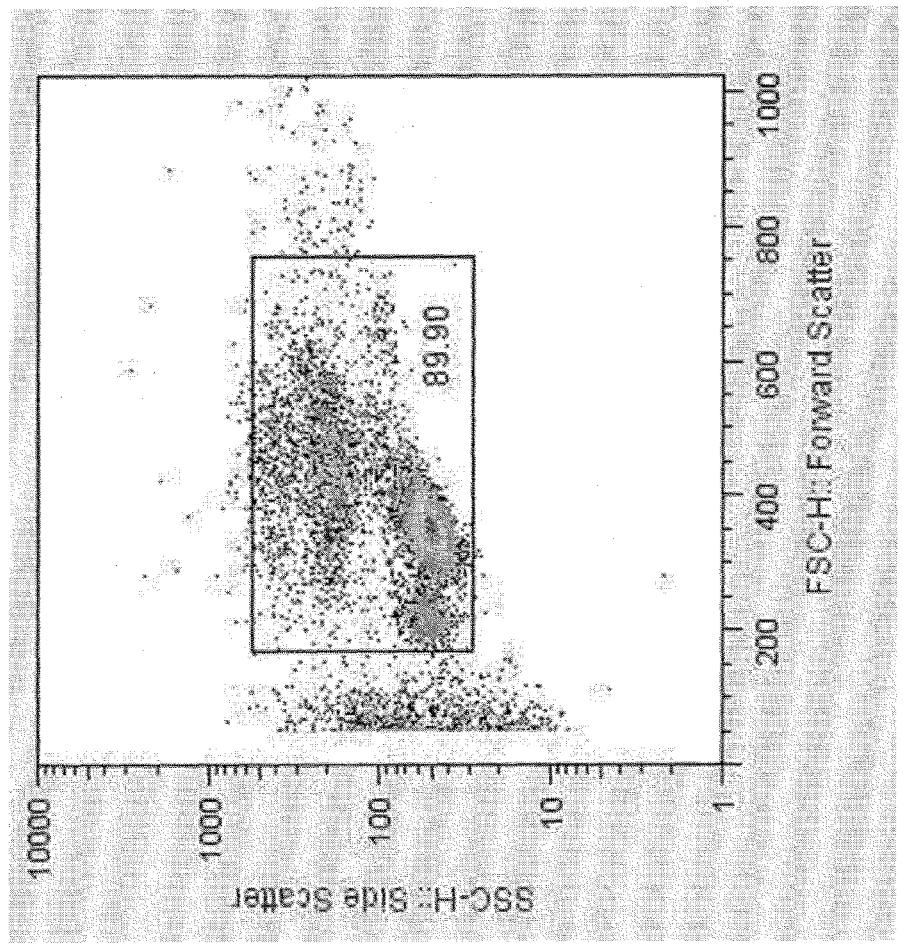
FIG. 1 is a dotplot of data from FACS analysis of hAMSC suspension, showing a gating based on forward and side scattering parameters. Similar gates were used in other FACS analysis provided herein.

Substantially homogeneous cellular compositions of mesenchymal stem cells enriched for HLA-G+ (HLA-G+ MSC), HLA-E+ (HLA-E+ MSC), or both HLA-G and HLA-E (HLA-G+/HLA-E+ MSC) are provided. The cells of the invention find use in therapeutic methods, e.g. as immunomodulatory agents, e.g. for co-transplantation with a source of hematopoietic stem cells, with solid tissue transplantation; and the like. In some embodiments, a nucleic acid construct is introduced into a population of cells comprising HLA-G+ MSC, HLA-E+ MSC or HLA-G+/HLA-E+ MSC. In a preferred embodiment, the nucleic acid construct encodes for HLA-G.

These cells find use for the reconstitution of mesenchymal tissues, for the long-term delivery of proteins expressed by the cells, and in transplantation with respect to hematopoietic support, immunoregulation, graft facilitation, and gene therapy. HLA-G+ MSC may enhance the ability of the bone marrow microenvironment to support hematopoiesis after stem cell transplantation. These cells may also suppress T cell activation without inducing allogeneic anergy. These findings may have important applications for stem cell transplantation, organ transplantation, and other regenerative and reparative therapies.

Definitions

Terms used in the claims and specification are defined as set forth below unless otherwise specified.

The term "ameliorating" refers to any therapeutically beneficial result in the treatment of a disease state, e.g., an autoimmune disease state, including prophylaxis, lessening in the severity or progression, remission, or cure thereof.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to alter a protein expression profile.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an," and "the" include plural referents unless the context clearly dictates otherwise.

HLA-G. As used herein, the term HLA-G refers to any one of the seven alternatively spliced transcripts and gene products (e.g., intracellular protein, cell surface marker, soluble protein) of the human HLA-G locus, including any of the polymorphisms at this locus, e.g. G*0105N. The full length isoform, HLA-G1, is listed in Genbank at accession number NM_002127, and the protein at accession NP_002118.1. The G2 isoform lacks exon 3. The G3 isoform lacks exons 3 and 4. HLA-G5 and HLA-G6 are soluble forms of HLA-G1 and HLA-G2, which include intron 4 sequences encoding a unique 21 amino acid. HLA-G3 results from the removal of exons 3 and 4.

The genome locus for HLA-G may be accessed at Genbank, accession NG_002398, and is referenced in Robinson and Marsh (2000) Rev Immunogenet 2 (4), 518-531; Beck and Trowsdale (2000) Annu Rev Genomics Hum Genet 1, 117-137; Rhodes and Trowsdale (1999) Rev Immunogenet 1 (1), 21-31; and Trowsdale (1993) Trends Genet. 9 (4), 117-122.

HLA-G1 belongs to the HLA class I heavy chain paralogues. This class I molecule is a heterodimer consisting of a heavy chain and a light chain (beta-2 microglobulin). The heavy chain is anchored in the membrane. HLA-G is expressed on fetal derived placental cells. The heavy chain is approximately 45 kDa and its gene contains 8 exons. Exon one encodes the leader peptide, exons 2 and 3 encode the alpha1 and alpha2 domain, which both bind the peptide, exon 4 encodes the alpha3 domain, exon 5 encodes the transmembrane region, and exon 6 encodes the cytoplasmic tail.

References relating to the sequence of HLA-G, each of which are herein specifically incorporated by reference particularly for the teaching of HLA-G sequences, include Yie et al. (2006) Hum. Reprod. 21 (10), 2538-2544; Cirulli et al. (2006) Diabetes 55 (5), 1214-1222; Hviid et al. (2006) Sarcoidosis Vasc Diffuse Lung Dis 23 (1), 30-37; Hviid et al. (2006) Hum. Immunol. 67 (1-2), 53-62; Ishitani et al. (1992) Proc. Natl. Acad. Sci. U.S.A. 89 (9), 3947-3951; Pook et al. (1991) Hum. Immunol. 32 (2), 102-109; Zemmour et al. (1991) Hum. Immunol. 31.

HLA-E. As used herein, the term HLA-E refers to any transcript and gene product (e.g., intracellular protein, cell surface marker, soluble protein) of the human HLA-E locus, including any of the polymorphisms at this locus (see, e.g., Geraghty et al. (1992) *Hum. Immunol* 33:174-84). HLA-E is listed in Genbank at accession number NM_005516.4, and the protein at accession NP_005507.3.

Indoleamine-pyrrole 2,3 dioxygenase or INDO. As used herein, the term Indoleamine-pyrrole 2,3 dioxygenase or INDO refers to any transcript and gene product (e.g., intracellular protein, cell surface marker, soluble protein) of the human INDO locus, including any of the polymorphisms at this locus. INDO is listed in Genbank at accession number NM_002164.4, and the protein at accession number NP_002155.1.

CD200. As used herein, the term CD200 refers to any transcript and gene product (e.g., intracellular protein, cell surface marker, soluble protein) of the human CD200 locus, including any of the polymorphisms at this locus. CD200 is listed in Genbank at accession number NM_005944.5, and the protein at accession number NP_001004196.2.

CD47. As used herein, the term CD47 refers to any transcript and gene product (e.g., intracellular protein, cell surface marker, soluble protein) of the human CD47 locus, including any of the polymorphisms at this locus. CD47 is listed in Genbank at accession number NM_001777.3 (variant 1) or NM_198793.2 (variant 2), and the protein at accession NP_001768.1.

CD271. As used herein, the term CD271 (also known as nerve growth factor receptor; NGFR) refers to any transcript and gene product (e.g., intracellular protein, cell surface marker, soluble protein) of the human CD271 locus, including any of the polymorphisms at this locus. CD271 is listed in Genbank at accession number NM_002507.2, and the protein at accession NP_002498.1

CD140b. As used herein, the term CD140b (also known as platelet derived growth factor receptor, beta polypeptide; PDGFRB) refers to any transcript and gene product (e.g., intracellular protein, cell surface marker, soluble protein) of the human CD140b locus, including any of the polymorphisms at this locus. CD140b is listed in Genbank at accession number NM_002609.3, and the protein at accession NP_002600.1

Mesenchymal Stem Cell (MSC). As used herein, the term MSC refers to a cell capable of giving rise to differentiated cells in multiple mesenchymal lineages, specifically to osteoblasts, adipocytes, myoblasts and chondroblasts. Generally, mesenchymal stem cells also have one or more of the following properties: an ability to undergo asynchronous, or asymmetric replication, that is where the two daughter cells after division can have different phenotypes; extensive self-renewal capacity; and clonal regeneration of the tissue in which they exist, for example, the non-hematopoietic cells of bone marrow. "Progenitor cells" differ from stem cells in that they typically do not have the extensive self-renewal capacity. In contrast to previously reported MSC and multipotent mesenchymal cell populations, the cells of the invention do not require lengthy time in culture prior to the appearance of the MSC phenotype, i.e. cells with the MSC phenotype and are responsive to canonical wnt signaling pathways are present in freshly isolated or primary cultures that have been cultured for less than about 20 passages; usually less than about 10 passages.

MSC have been harvested from the supportive stroma of a variety of tissues. In both mouse and human a candidate population of cells has been identified in subcutaneous adipose tissue (AMSC). These cells have demonstrated the same in vitro differentiation capacity as BM-MSC for the mesenchymal lineages, osteoblasts, chondrocytes, myocytes, neurons, and adipocytes (Zuk et al. (2002) Mol Biol Cell 13, 4279-95; Fujimura et al. (2005) Biochem Biophys Res Commun 333, 116-21). Additionally, cell surface antigen profiling of these cells has revealed similar cell surface marker characteristics as the more widely studied BM-MSC (Simmons et al. (1994) Prog Clin Biol Res 389, 271-80; and Gronthos et al. (2001) J Cell Physiol 189, 54-63).

MSC may be characterized by both the presence of cell surface markers associated with specific epitopes identified by antibodies and the absence of certain cell surface markers as identified by the lack of binding of specific antibodies. MSC may also be identified by functional assays both in vitro and in vivo, particularly assays relating to the ability of stem cells to give rise to multiple differentiated progeny; assays for responsiveness to canonical wnt signaling; and the like.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The cells which are employed may be fresh, frozen, or have been subject to prior culture. They may be fetal, neonate, adult. MSC may be obtained from adipose tissue (see U.S. Patent application 20030082152); bone marrow (Pittenger et al. (1999) Science 284(5411):143-147; Liechty et al. (2000) Nature Medicine 6:1282-1286); G-CSF or GM-CSF mobilized peripheral blood (Tondreau et al. (2005) Stem Cells 23(8): 1105-1112), or any other conventional source.

The methods of the invention provide for substantially homogeneous cellular compositions of MSC enriched for HLA-G+ MSC and/or HLA-E+ MSC. In such compositions, the MSC having an HLA-G$^+$ and/or HLA-E$^+$ phenotype may be at least about 10% or 15% of the total number of cells, at least about 25% of the total number of cells, at least about 50% of the total number of cells; at least about 75% of the total number of cells; at least about 85% of the total number of cells; at least about 90% or 95% of the total number of cells; or more.

In some embodiments, the homogeneous cellular composition of MSC is stable in non-differentiating culture conditions, where the proportion of cells in the composition that have an MSC phenotype are maintained over multiple passages. Such cells may be maintained for at least about two passages; at least about five passages; at least about ten passages; or more.

Non-differentiating culture conditions. MSC as described above can be propagated continuously in culture, using culture conditions that promote proliferation without promoting differentiation, using methods known in the art. The cells can be maintained in medium, e.g. DMEM; RPMI; etc. in the presence of fetal bovine serum or serum-free replacement without differentiation. Generally the cells are passaged at about 75 to 95% confluence, using a protease, e.g. trypsin, collagenase, etc.

Differentiating culture conditions. Differentiating cells are obtained by culturing or differentiating MSC in a growth environment that enriches for cells with the desired phenotype, e.g. osteoblasts, adipocytes, etc. The culture may comprise agents that enhance differentiation to a specific lineage.

Osteogenic differentiation may be performed by plating cells and culturing to confluency, then culturing in medium comprising β-glycerol phosphate, ascorbic acid and retinoic acid (see Cowan et al. (2005) Tissue engineering 11, 645-658).

Adipogenic differentiation may be performed by plating cells and culturing to confluency, then culturing in medium comprising dexamethasone, indomethacin, 3-isobutyl-1-methylxanthine (IBMX), and insulin, then maintaining in growth media with 1 insulin.

Myocyte differentiation may be performed by plating cells and culturing to confluency, then culturing in medium comprising horse serum, dexamethasone, and hydrocortisone (see Eun et al. (2004) Stem Cells 22:617-624); or 5-azacytidine (see Fukuda et al. (2001) Artificial Organs 25:187).

Chondrocyte differentiation may be performed by plating cells and culturing to confluency, then culturing in medium comprising dexamethasone, ascorbic acid 2-phosphate, insulin, transferrin, selenous acid, with or without TGF-$β_1$ (see Williams et al. (2003) Tissue Engineering 9(4):679).

Following the differentiation in culture, the culture will usually comprise at least about 25% of the desired differentiated cells; more usually at least about 50% differentiated cells cells; at least about 75% differentiated cells, or more. The cells thus obtained may be used directly, or may be further isolated, e.g. in a negative selection to remove MSCs and other undifferentiated cells. Further enrichment for the desired cell type may be obtained by selection for cell surface markers characteristic of the cells, e.g. by flow cytometry, magnetic bead separation, panning, etc., as known in the art.

Isolation and Characterization of MSC Expressing HLA-$G^+$ and/or HLA-$E^+$

In mesenchymal cell populations derived from humans, it is shown herein that there is a subpopulation of stem cells that express endogenous HLA-G and/or HLA-E. These cells may be responsible for immune regulatory functions of MSC. In some embodiments, mesenchymal stem cells as described herein may also express additional markers, e.g., Indoleamine-pyrrole 2,3-dioxygenase (INDO), CD200, CD47, CD271, CD140b, etc. The HLA-$G^+$ MSC, HLA-$E^+$ MSC, and HLA-$G^+$/HLA-$E^+$ MSC may be identified by their phenotype with respect to particular cell surface markers (e.g., HLA-G, HLA-E, CD200, CD47, etc), and/or by their functional phenotype (e.g., expression of INDO). In some embodiments, the HLA-$G^+$ MSC, HLA-$E^+$ MSC, or HLA-$G^+$/HLA-$E^+$ MSC are identified and/or isolated by binding to the cell with reagents specific for the cell surface markers of interest. In some embodiments, the reagents specific for the cell surface markers of interest are antibodies, which may be directly or indirectly labeled. Such antibodies will usually include antibodies specific for HLA-G, antibodies specific for HLA-E, etc.

Analysis or separation by cell staining may use conventional methods, as known in the art. Techniques providing accurate enumeration include confocal microscopy, fluorescence microscopy, fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, polynucleotide probes specific for an mRNA of interest, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each cell surface marker.

The antibodies are added to cells, and incubated for a period of time sufficient to bind the available antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

Provided herein are methods of isolating mesenchymal stem cells (MSC) selected from the group consisting of HLA-G+ MSC, HLA-E+ MSC, and HLA-G+/HLA-E+ MSC, the method comprising contacting a population of MSC with an antibody specific for HLA-G for a period of time sufficient to bind said HLA-G and selecting for cells expressing said HLA-G. In one embodiment, the isolation of a cell population as described herein may comprise utilizing a combination of an antibody which recognizes HLA-G and one or more antibodies that recognize a well-known marker on mesenchymal stem cells. One method for such preparation of the precursor cells of the present invention is to first select a population of cells expressing a marker identifying mesenchymal stem cells, for example, SH3 or SH2 by immunomagnetic selection of adipose tissue and/or a low density human bone marrow cell sample (see, e.g., Buhring et al. (2007) "Novel Markers for the Prospective Isolation of Human MSC" Ann. N.Y. Acad. Sci. 1106:262-271). Alternatively, it is contemplated that the initial cell selection can be based on the HLA-G cell surface marker and may be optionally further characterized using monoclonal antibodies to other known MSC markers, which may include one or more of the MSC markers described herein (e.g., HLA-E+, INDO, CD200, CD47, CD271, CD140b, etc).

The cells of interest may be separated from a complex mixture of cells by techniques that enrich for cells having the above described characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for MSC expressing HLA-G+ and/or HLA-E+ are achieved in this manner. Thus, certain mesenchymal stem cell population embodiments described herein are identified by FACS by the relative brightness of immunofluorescent stained antibodies bound thereto as either or both HLA-G+ and HLA-E+. Such HLA-G+ and/or HLA-E+ positive MSC as described herein may also be optionally positive for INDO, CD200, CD47. Further, such HLA-G+ and/or HLA-E+MSC may also be positive for MSC markers known in the art, e.g., CD271, and/or CD140b.

The subject population may be at or about 10 or 25% of the cell population, more usually at least about 40% of the cell population, preferably at least about 50% of the cell composition, still more preferably at least about 75% of the cell composition, and most preferably at least about 90% or more. The desired cells are identified by their surface phenotype, by the ability to self-renew, etc. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for the MSC may be used in a variety of screening assays and cultures, as described below.

The enriched HLA-G+ MSC, HLA-E+ MSC, or HLA-G+/HLA-E+ population may be maintained and/or expanded in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc.

In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977] *J Exp Med* 145:1612-1616); and heterogeneous thymic stromal.

Genetic Manipulation of MSC Expressing HLA-G and/or HLA-E

In one embodiment of the invention, an exogenous nucleic acid (e.g., a nucleic acid construct comprising a vector, inducible promoter, a sequence encoding a protein product of interest, etc.) is introduced into a population of MSC as described herein (e.g., HLA-G+ MSC, HLA-E+ MSC, HLA-G+/HLA-E+ MSC). A variety of vectors (e.g., plasmids, expression vectors, retroviral vectors, etc.) are known in the art for the delivery of sequences into a cell. In a preferred embodiment, the vector is a retroviral or lentiviral vector. For example, see Baum et al. (1996) J Hematother 5(4):323-9; Schwarzenberger et al. (1996) Blood 87:472-478; Nolta et al. (1996) P.N.A.S. 93:2414-2419; and Maze et al. (1996) P.N.A.S. 93:206-210, Mochizuki et al. (1998) J Virol 72(11):8873-83. The use of adenovirus based vectors with hematopoietic cells has also been published, see Ogniben and Haas (1998) *Recent Results Cancer Res* 144:86-92.

Various techniques known in the art may be used to transfect the target cells, e.g. electroporation, calcium precipitated DNA, fusion, transfection, lipofection and the like. The particular manner in which the DNA is introduced is not critical to the practice of the invention.

Combinations of retroviruses and an appropriate packaging line may be used, where the capsid proteins will be functional for infecting the target cells. Usually, the cells and virus will be incubated for at least about 24 hours in the culture medium. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the β-catenin gene after integration into a target cell genome. For some uses, however, it is desirable to have a regulatable promoter driving expression. Where such a promoter is included, the promoter function of the LTR will be inactivated. This is accomplished by a deletion of the U3 region in the 3' LTR, including the enhancer repeats and promoter, which is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL-2 promoter in T cells, immunoglobulin promoter in B cells, etc.

An ordinarily skilled artisan will recognize the well-known methods of obtaining a sequence encoding a protein product of interest, e.g., isolation and/or amplification of the sequence from a particular population of cells, chemical synthesis, etc. In some embodiments, protein products of interest include growth factors or a combination of growth factors, e.g., for the reconstruction of damaged tissue. In other embodiments, suitable sequences encoding a protein product of interest include those that encode well-known immunosuppressive proteins (e.g., CLTA-4, TGF-β, etc) and/or may aid in suppressing the immune response toward specific antigens, e.g., autoantigens, alloantigens, etc. (see, e.g., U.S. Pat. No. 6,797, 269). Additionally, and without being bound by mechanism, it is expected that the mesenchymal stem cell population expressing endogenous HLA-G and/or HLA-E described herein are less susceptible to HLA-G gene repression (see, e.g., Moreau et al. (2003) *PNAS* 100:1191-1196). Accordingly, in certain preferred embodiments, an MSC population expressing HLA-G and/or HLA-E as described herein is genetically modified by introduction of an exogenous nucleic acid comprising a sequence encoding HLA-G.

Protein products of interest may also be selected to aid in detecting and/or selecting for MSC cell populations as described herein. For detecting or selecting stem cells, the detection construct is introduced into a cell or population of cells, suspected of being or comprising stem cells. After introduction of the expression construct, the cells are maintained for a period of time sufficient to express the detectable marker, usually at least about 12 hours and not more than about 2 weeks, and may be from about 1 day to about 1 week.

Genetic constructs may be removed from the target cells after expansion. This can be accomplished by the use of a transient vector system, or by including a heterologous recombination site that flanks the desired protein coding sequence. Preferably a detectable marker, e.g. green fluorescent protein, luciferase, cell surface proteins suitable for antibody selection methods, etc. is included in the expression vector, such that after deletion of the construct the cells can be readily isolated that lack the exogenous sequence. The term "heterologous recombination site" is meant to encompass any introduced genetic sequence that facilitates site-specific recombination. In general, such sites facilitate recombination by interaction of a specific enzyme with two such sites. Exemplary heterologous recombination sites include, but are not necessarily limited to, lox sequences with recombination mediated by Cre enzyme; frt sequences (Golic et al. (1989) *Cell* 59:499-509; O'Gorman et al. (1991) *Science* 251:1351-5; recombination mediated by the FLP recombinase), the recognition sequences for the pSR1 recombinase of *Zygosaccharomyces rouxii* (Matsuzaki et al. (1990) *J. Bacteriol* 172: 610-8), and the like.

Expression vectors that provide for the transient or long term expression in mammalian cells may be used. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient short term expansion of cells, but do not affect the long term genotype of the cell.

In some embodiments, the selected cells are maintained in culture for at least one passage, usually at least about two passages; at least about three passages; or more, and not more than about 10 passages, usually not more than about seven passages. Following such culture, the cells are sorted for expression of the detectable marker as described above. It has been found that such cultured and resorted cells have an unexpectedly stable maintenance of the MSC phenotype.

The stem cells isolated by the methods of the invention, and cells and animals generated by introduction of an immortalizing construct find use in compound screening, for the identification of genes expressed in stem cells, for therapies utilizing stem cells, and the like.

Genetic Screening

The enriched compositions of HLA-G$^+$ MSC, HLA-E$^+$ MSC, or HLA-G$^+$/HLA-E$^+$ MSC are also useful as a source of respective HLA-G$^+$ MSC, HLA-E$^+$ MSC, HLA-G$^+$/HLA-E$^+$ MSC specific genetic material, particularly mRNA transcripts (e.g., for the preparation of sequences encoding a protein product of interest). A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample.

A number of methods are available for analyzing nucleic acids for the presence of a specific sequence, e.g. upregulated or downregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. ALEXA dyes (available from Molecular Probes, Inc.); fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence.

Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes is then contacted with the cells and the probes allowed to hybridize. Excess probe is digested, washed away and the amount of hybridized probe measured. This approach is described in greater detail by Nucleic Acid Hybridization: A Practical Approach (Hames, et al., eds., 1987).

A variety of so-called "real time amplification" methods or "real time quantitative PCR" methods can also be utilized to determine the quantity of mRNA present in a sample. Such methods involve measuring the amount of amplification product formed during an amplification process. Fluorogenic nuclease assays are one specific example of a real time quantitation method that can be used to detect and quantitate transcripts. In general such assays continuously measure PCR product accumulation using a dual-labeled fluorogenic oligonucleotide probe—an approach frequently referred to in the literature simply as the "TaqMan" method. Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, each of which is incorporated by reference in its entirety.

Methods of Transplantation

The substantially homogeneous HLA-G$^+$ MSC compositions of the invention find use in the treatment of degenerative diseases, and the immunomodulation of transplantation, and may be delivered as progenitor cells; as differentiated progeny thereof, e.g. after commitment to a lineage of interest; and/or as a means of delivering gene products to the affected area.

A cell transplant, as used herein, is the transplantation of one or more cells into a recipient body, usually for the purpose of augmenting function of an organ or tissue in the recipient. As used herein, a recipient is an individual to whom tissue or cells from another individual (donor), commonly of the same species, has been transferred. The graft recipient and donor are generally mammals, preferably human. Laboratory animals, such as rodents, e.g. mice, rats, etc. are of interest for drug screening, elucidation of developmental pathways, etc.

For the purposes of the invention, the cells may be allogeneic, autologous, or xenogeneic with respect to the recipient. MSC expressing HLA-G and/or HLA-E$^+$ as described herein are at least partially protected from immune rejection, and therefore a perfect match of histocompatibility antigens is not required for allogeneic transplantation. At least one HLA match may be provided, at least two matches, three matches, four matches, five matches, or more. The number of cells to be transplanted will vary with the specific treatment that is desired, the size of the recipient, and the like. In general, for a human, at least about $10^4$ cells/KG will be administered; at least about $10^5$; at least about $10^6$; at least about $10^7$; or more.

Where the transplantation is intended for the treatment of degenerative disease, e.g. osteogenesis imperfecta; repair of mesenchymal tissues; etc., the cells are administered in a manner that permits them to graft or migrate to the intended tissue site and reconstitute or regenerate the functionally deficient area. MSCs find use for engineering cartilage, growth plate, bone and tendon/ligament as well as the clinical trial of autologous chondrocyte implantation (see, for example, Hui et al. (2005) Ann Acad Med Singapore).

Genetically engineered mesenchymal stem cells can be used to target gene products, e.g. to sites of degeneration. These gene products can include survival-promoting factors to rescue bone or cartilage, factors that can act in an autocrine manner to promote survival and differentiation of grafted cells. Therapy using MSC engineered to synthesize a growth factor or a combination of growth factors can not only ensure sustained delivery of factors, but may also reconstruct damaged tissue. For example, it has been shown that human mesenchymal stem cells ectopically expressing full-length dystrophin can complement Duchenne muscular dystrophy myotubes by cell fusion (Goncalves et al. (2006) Hum Mol Genet. 15(2):213-21).

Compositions and methods are provided for increasing the survival of cells during the process of transplantation. Cells to be transplanted are administered together with the substantially homogeneous mesenchymal stem cell compositions of the invention. MSC have immunomodulatory effects, enhance hematopoietic engraftment in recipients of autologous and allogeneic grafts; inhibit T-cell proliferation in mixed lymphocyte cultures, prolong skin allograft survival, and can decrease graft-versus-host disease (GVHD) when co-transplanted with hematopoietic stem cells. MSCs induce their immunosuppressive effect via a soluble factor. In allogeneic stem cell transplantation, MSCs are used for hematopoiesis enhancement, as GVHD prophylaxis, and for the treatment of severe acute GVHD. They are also of use in the treatment of organ transplant rejection and in autoimmune inflammatory bowel disorders where immunomodulation and tissue repair are needed (see Le Blanc and Ringden (2005) Biol Blood Marrow Transplant. 11(5):321-34). The cells of the invention may be administered before transplantation, at the same time, or following transplantation.

The compositions of the invention provide for increased survival of transplanted cells after they are transferred to a recipient animal. In experimental systems, survival of cells may be measured after short periods of time, e.g. after at least about three to about seven days. When measured over such a time period, the methods of the invention provide for an increase in cell survival of at least about 5-fold, at least about 10-fold, at least about 20-fold, at least about 50-fold, at least about 100-fold, or more, relative to transplantation in the absence of the MSCs.

Cells of interest for transplantation include, without limitation, cardiomyocytes and progenitors thereof; neural progenitor cells, e.g. for the regeneration of neurons, or retina, and the like; pancreatic islet cells, particularly pancreatic β-cells; hematopoietic stem and progenitor cells; muscle satellite cells; endothelial cells or progenitors thereof; and the like. Tissues of interest include liver tissue, kidney tissue, heart tissue, lung tissues, skin tissue, brain tissue; spinal cord tissue; pancreatic islets; retinal tissue; and the like.

In the methods of the invention, cells to be transplanted are transferred to a recipient in any physiologically acceptable excipient comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing. If frozen, the cells may be stored in a 10% DMSO, 50% FCS, 40% RPMI 1640 medium.

Kits

The formulations of the invention are optionally packaged in a suitable container with written instructions for a desired purpose. Such formulations may comprise a vector, in a form suitable for combining with cells prior to selection. Such a composition may further comprise suitable buffers and/or excipients appropriate for culture.

For further elaboration of general techniques useful in the practice of this invention, the practitioner can refer to standard textbooks and reviews in cell biology, tissue culture, and embryology. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Other features and advantages of the invention will be apparent from the description of the preferred embodiments, and from the claims. The following examples are offered by way of illustration and not by way of limitation.

EXPERIMENTAL

Example 1

Human Adipose MSC Harvest & Isolation

Human Adipose Mesenchymal Stem Cell Isolation. MSCs were isolated from human fat tissue. After isolation, they were cultured in DMEM (containing high glucose, sodium pyruvate and Glutamax)+10% FBS+1% PS and were let to grow to ~90% confluency before injection, splitting or freezing. 300 ml of lipoaspirate is settled above the blood fraction, shaken with an equivalent volume of HBSS with 1% antibiotics and allowed to settle above the HBSS, with the HBSS then removed. The washing step is repeated until the final wash medium is clear. Where tissue is used, the fat is washed with sequential dilutions of betadine in PBS, then chopped. The lipoaspirate or fat tissue is digested with collagenase to completion, then separated through a large bore filter to separate the undigested tissue. The cells are centrifuged, and the floating adipocytes, lipids and the digestion medium aspirated off. RBC are lysed, then the remaining cells washed in PBS. For culture, the cells are counted and resuspended in the appropriate concentration and medium.

In-vivo Injections. For injection experiments, cells were detached from the dishes with 0.025% Trypsin-EDTA and re-suspended in PBS+3% FBS. The cells were passed through a 40 μm filter to separate cell aggregates and were suspended again in PBS+3% FBS at a concentration of approximately $5 \times 10^5$ cells per ml ($10^5$ cells per 200 μl). They were stored in sterile eppendorf tubes on ice to be transported to animal facility. The time interval between cell preparation and injections was 30 minutes on average but not more than 45 minutes. Jurkat and HSCs were prepared in a similar way except that these cells grow in suspension and do not require detachment with Trypsin.

Cells were injected into 7 week old female FVB mice through tail vein injection. At 1 and 2 weeks post injection 200 μl of blood was collected from mice through retro orbital plexus under anesthesia with isoflurane. The blood was stored in heparinized tubes on ice for further processing and FACS analysis.

FACS Analysis for Survival Studies. Indirect labeling requires two incubation steps; one with a primary antibody then the next one with a compatible secondary antibody. The secondary (and not the primary) antibodies have the fluorescent dye (FITC, PE, Cy5, etc.) attached. 1. Harvest, wash the cells and determine the total cell number. Use polystyrene round-bottom 12×75 mm Falcon tubes for Flow cytometry/FACS analysis. It is always useful to check the viability of the cells which should be around 95% not less than 90%. 2. Resuspend the cells approximately $1-5 \times 10^7$ cells/ml in ice cold 3% BSA/PBS. 3. Add 100 μl of cell suspension to each Falcon tube. 4. Add 0.1-10 μg/ml of the primary antibody. Dilutions, if necessary, should be made in 3% BSA/PBS. 5. Incubate for at least 30 min at room temperature. 6. Wash the cells 3-times by centrifugation at 400 g for 5 min and resuspend them in ice cold PBS. 7. Dilute the fluorochrome-labeled secondary antibody in 3% BSA/PBS at the optimal dilution (according to the manufacturer's instructions) and then resuspend the cells in this solution. 8. Incubate for at least 20 minutes at room temperature in the dark. 9. Wash the cells 3-times by centrifugation at 400 g for 5 min and resuspend them in ice cold PBS. The cells are now ready for analysis by flow cytometry. 10. After the last step, centrifuge the cells and remove the liquid. 11. Add 0.5 to 1.0 ml of cold 0.5% paraformaldehyde solution and vortex immediately. 12. Store the cell suspension at 4° C. in the dark.

RBCs were lysed using RBC lysis buffer from eBiosciences according to manufacturer's instructions. A cell count was performed and the cells were incubated in the primary anti human HLA-Class I antibody from Abcam. The cells in the negative control sample were not incubated with the primary antibody and were kept in PBS+3% FBS on ice.

Figure 3:
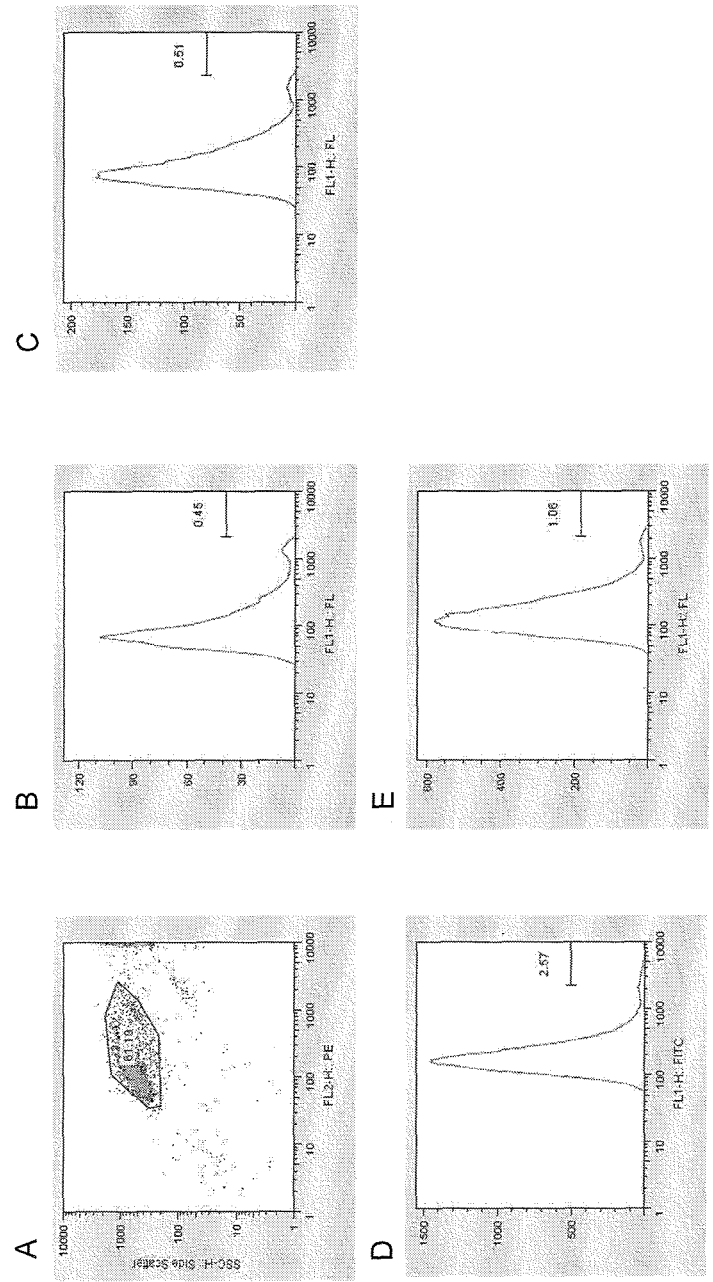
FIGS. 3A-3E are histograms of fluorescence profiling from human adipose mesenchymal stem cells (hAMSC) stained with propidium iodide for exclusion of dead cells (A), no antibody for control (B), isotype antibody for control (C) anti-HLA-G antibody (D) or anti HLA-E antibody (E).

Similar gates were used for the analysis shown in FIG. 3. FIGS. 3B and 3C are histograms of control cells, i.e., cells stained with no antibody (FIG. 3B) or with isotype control antibody (FIG. 3C).

Mesenchymal stem cells isolated from adipose tissue (AMSC) or bone marrow (BMSC) were evaluated by FACS for expression of HLA-G and HLA-E immediately after isolation (P0) or after being cultured for up to 7 passages (P1-P7), in the absence or presence of 200 nl/ml IFNγ (+IFNγ). The percentage of cells positive for HLA-G or HLA-E are shown in Table 1 below.

TABLE 1

| | | P0 | P1 | P2 | P3 | P4 | P5 + IFNγ 200 ng/ml |
|---|---|---|---|---|---|---|---|
| HLA-G in % | AMSC prep1 | 0.35 | 0.51 | 0.41 | 0.23 | 0.06 | 0.16 |
| | AMSC prep2 | 0.53 | 0.22 | 0.11 | 0.19 | 0.13 | 0.19 |
| | AMSC prep3 | | 0.53 | 0.14 | 0.21 | 0.07 | 0.08 |
| HLA-E in % | AMSC prep1 | 0.43 | 0.22 | 0.03 | 0.00 | 0.00 | 0.00 |
| | AMSC prep2 | 0.32 | 0.19 | 0.09 | 0.01 | 0.02 | 0.00 |
| | AMSC prep3 | | 0.31 | 0.05 | 0.04 | 0.01 | 0.00 |

| | | P5 | P6 + IFNγ | P7 + IFNγ |
|---|---|---|---|---|
| HLA-G in % | BMSC | 0.18 | 0.22 | 0.14 |
| HLA-E in % | | 0.02 | 0.01 | 0.00 |

After 40 minutes, cells were washed with PBS for 3 times. Then, all samples including the negative control samples were incubated with the secondary antibody conjugated to FITC. All antibodies were used at concentrations recommended by the manufacturer. After incubation for 30 minutes, cells were washed again with PBS for 3 times, re-suspended in 200 µl PBS+3% FBS and stored on ice for transfer to FACS facility. Data regarding >10,000 events for each sample were collected using CellQuest software and analyzed by Flowjo V 7.1.

To eliminate debris, dead cells and cell aggregates data from FACS analysis, we used a gating based on forward and side scattering parameters to collect data as shown in FIG. 1. Similar gates are used for all other analyses.

Figure 2:
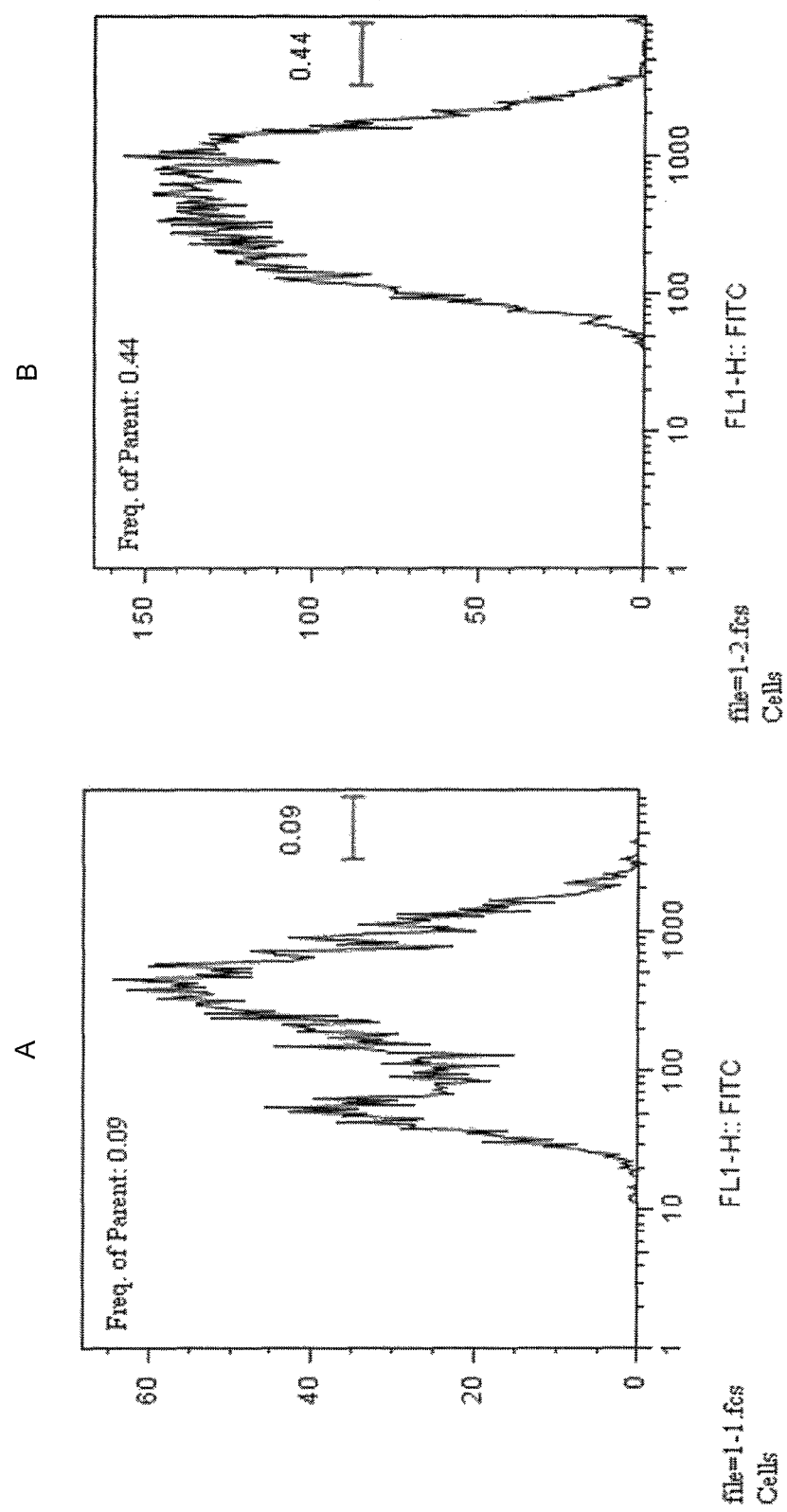
FIGS. 2A-2B are histograms of fluorescence profiling from human adipose mesenchymal stem cells (hAMSC) stained with secondary antibody only (A), or an antibody specific for HLA-G (B).

FACS Analysis or Sorting for HLA-G and/or HLA-E expression. Human adipose mesenchymal stem cells hAMSCs isolated with the procedure described above were let to grow to passage 1 in DMEM (containing high glucose, sodium pyruvate and Glutamax)+10% FBS+1% PS to a confluency of ~90%. They were detached from the dishes with 0.025% Trypsin-EDTA and re-suspended in PBS+3% FBS. The cells were passed through a 40 µm filter to separate cell aggregates and were suspended again in PBS+3% FBS at a concentration of approximately $10^6$ cells per 100 µl. Mouse anti HLA-G or mouse anti-HLA-E antibody was used as a primary antibody and anti-Mouse IgG antibodies conjugated to FITC was used as a secondary antibody. All three antibodies were purchased from Abcam (Cambridge, Mass.). The cells were analyzed by the same software/gating mentioned above. The results of the HLA-G staining are shown in FIGS. 2A-2B and FIG. 3D. The results of the HLA-E staining are shown in FIG. 3E.

FIG. 2A shows human mesenchymal stem cells (hAMSC) incubated with secondary antibody only; FIG. 2B is from cells incubated with primary and secondary antibodies. It was concluded that 0.35% of the population expresses HLA-G on its surface.

FIG. 3A shows human mesenchymal stem cells (hAMSC) stained with propidium iodide for the exclusion of dead cells.

Figure 4:
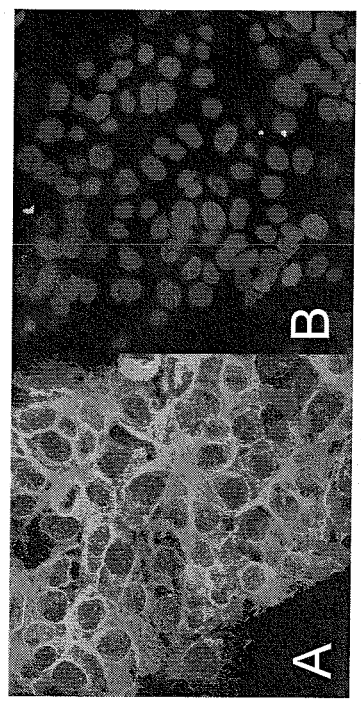
FIGS. 4A and 4B are immunohistochemistry slides of human adipose mesenchymal stem cells (AMSC) stained primarily with HLA-G (A) or isotype control antibody (B) and secondarily with anti-mouse FITC antibody and DAPI.

Immunocytochemistry experiments: Slide chambers were coated with poly-L-lysine for one hour at room temperature, washed thrice with sterile water, dried completely, and sterilized under ultraviolet light for at least 4 hours. Human adipose mesenchymal stem cells (hAMSC) were cultured on the slides to confluency, washed, fixed with ice-cold acetone, washed with phosphate buffered solution, and blocked with 5% goat serum in PBS. The cells were stained with microscopy by incubating the cells in diluted anti-HLA-G IgG (Santa Cruz) in a humidified chamber for 1 hour at room temperature, washing the cells thrice in PBS, incubating the cells with secondary antibody at room temperature for 1 hour in the dark, washing the cells with phosphate buffered solution three times, and incubating the cells with DAPI. FIG. 4 shows the results of hAMSC stained with anti-HLA-G antibody (FIG. 4A) or isotype control antibody (FIG. 4B).

Figure 5:
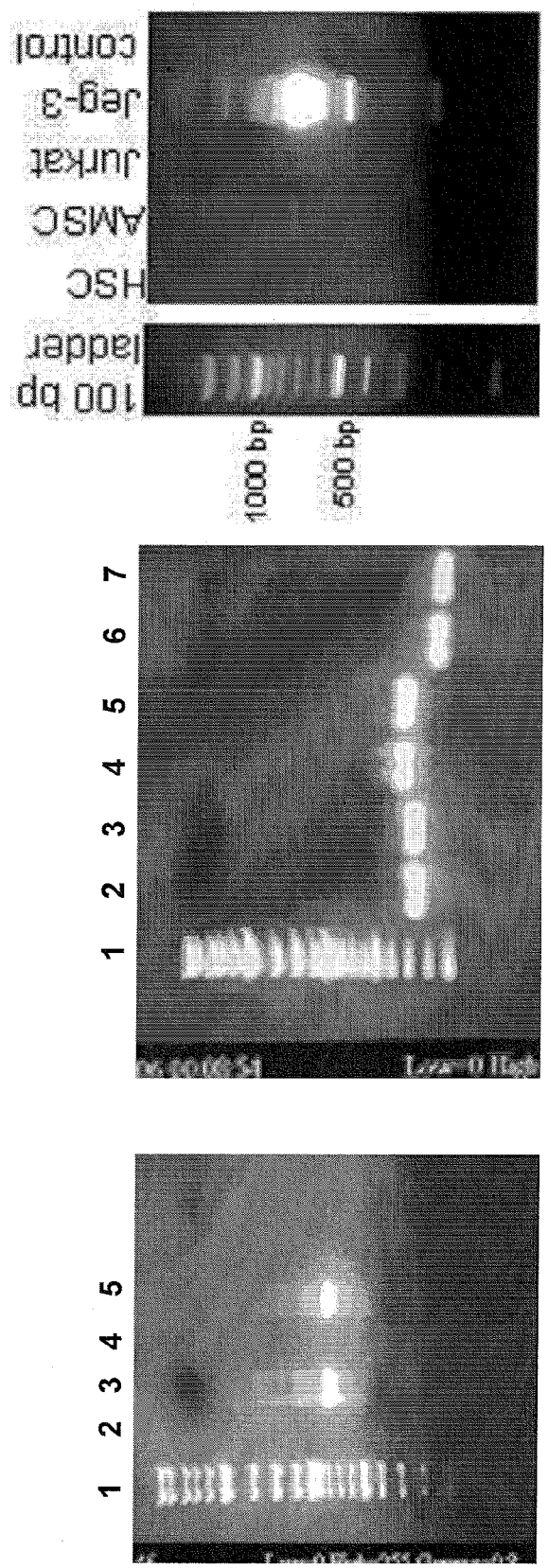
FIG. 5A is a gel of a molecular weight DNA ladder (lane 1), cDNA resulting from RT-PCR amplification of RNA isolated from Jeg-3 cells using primers specific for HLA-G (lane 3) or cDNA resulting from RT-PCR amplification of universal RNA using primers specific for HLA-G (lane 5). Lanes 2 and 4 are products resulting from control RT-PCR amplification (no primers) of RNA isolated from Jeg-3 cells or universal RNA.
FIG. 5B is a gel of a molecular weight DNA ladder (lane 1), cDNA resulting from RT-PCR amplification of universal RNA (lanes 2, 4, 6) or Jeg-3 cells (lanes 3, 5, and 7) using primers specific for HLA-A (lanes 2 and 3), HLA-B (lanes 4 and 5), or HLA-C (lanes 6 and 7).
FIG. 5C is PCR showing expression of HLA-G by human adipocyte mesenchymal cells (AMSC) and Jeg-3 cells but not human stem cells (HSC) or Jurkat cells.

RT-PCR experiments. RNA samples were extracted from MSCs sing the Qiagen RNeasy kit according to manufacturer's instructions. The primers included in the attached file were used to amplify the target genes. The protocols for PCR (for use with Qiagen Hotstart Highfidelity DNA Polymerase) and separation of amplicons on agarose gel are shown in FIG. 5. The primers were tested using cDNA synthesized from human universal RNA and Jeg-3 cells] HLA-G (+)]. The results are shown in FIGS. 5A-5B, where in FIG. 5A the lanes are: Ladder, Null, HLA-G from Jeg-3 Cells, HLA-G from universal RNA. In FIG. 5B the lanes are: Ladder, HLA-A from universal RNA, HLA-A from Jeg-3 Cells, HLA-B from universal RNA, HLA-B from Jeg-3 Cells, HLA-C from universal RNA, HLA-C from Jeg-3 Cells. FIG. 5C is PCR showing expression of HLA-G by human adipocyte mesenchymal cells and Jeg-3 cells but not human stem cells or Jurkat cells.

FIG. 6A-6C are gels of RT-PCR amplification products of from human adipose mesenchymal stem cells (hAMSC) freshly isolated (P0) once (P1), twice (P2), thrice (P3), four times (P4) or bone marrow stem cells (BMSC) passage four times (P4), five times (P5), six times (P6), seven times (P7) using primers specific for HLA-E or HLA-G (FIG. 6A) idoleamine-pyrrole 2,3 dioxygenase (INDO; FIG. 6B), CD271 or CD140b (FIG. 6C) in the absence or presence of Interferon-γ (IFN-γ).

Primers used were as follows. All the primers have a Tm very close to 60 C and the product sizes are between 100 to 300 base pairs.

| | |
|---|---|
| HLA-A Fwd: | GCGGCTACTACAACCAGAGC (SEQ ID NO: 1) |
| HLA-A Rev: | CCAGGTAGGCTCTCAACTGC (SEQ ID NO: 2) |
| HLA-B Fwd: | GACACCCAGTTCGTGAGGTT (SEQ ID NO: 3) |
| HLA-B Rev: | GATGTAATCCTTGCCGTCGT (SEQ ID NO: 4) |
| HLA-C Fwd: | GCGGCTACTACAACCAGAGC (SEQ ID NO: 5) |
| HLA-C Rev: | GATGTAATCCTTGCCGTCGT (SEQ ID NO: 6) |
| HLA-DP Fwd: | GACCTTCCAGATCCTGGTGA (SEQ ID NO: 7) |
| HLA-DP Rev: | CTTTCTTGCTCCTCCTGTGC (SEQ ID NO: 8) |
| HLA-DQ Fwd: | CAGATCAAAGTCCGGTGGTT (SEQ ID NO: 9) |
| HLA-DQ Rev: | TCACCAGGATCTGGAAGGTC (SEQ ID NO: 10) |
| HLA-DR Fwd: | CAGTTCCTCGGAGTGGAGAG (SEQ ID NO: 11) |
| HLA-DR Rev: | CTCAGCATCTTGCTCTGTGC (SEQ ID NO: 12) |
| HLA-E Fwd: | ATTTCCACACTTCCGTGTCC (SEQ ID NO: 13) |
| HLA-E Rev: | GCAGGTTCACTCGGAAAATC (SEQ ID NO: 14) |
| HLA-G Fwd: | CCACCACCCTGTCTTTGACT (SEQ ID NO: 15) |
| HLA-G Rev: | TGGCACGTGTATCTCTGCTC (SEQ ID NO: 16) |
| B-Act Fwd: | AAGTACTCCGTGTGGATCGG (SEQ ID NO: 17) |
| B-Act Rev: | CACCTTCACCGTTCCAGTTT (SEQ ID NO: 18) |
| CD47 Fwd: | TAACCTCCTTCGTCATTGCC (SEQ ID NO: 19) |
| CD47 Rev: | TCTCCAAATCGGAGTCCATC (SEQ ID NO: 20) |
| CD200 Fwd: | TACCTACAGCCTGGTTTGGG (SEQ ID NO: 21) |
| CD200 Rev: | TGGTTGAGTTTTGGAGTCCC (SEQ ID NO: 22) |
| INDO Fwd: | GCGCTGTTGGAAATAGCTTC (SEQ ID NO: 23) |
| INDO Rev: | CAGGACGTCAAAGCACTGAA (SEQ ID NO: 24) |

The instant application contains a Sequence Listing which has been submitted in ASCII format via EFS-Web and is hereby incorporated by reference in its entirety. Said ASCII copy, created on Apr. 22, 2011, is named 22008761.txt and is 5,751 bytes in size.

Injection into animals. Dosimetry showed that injection of 3 million cells led to immediate death in most cases. The maximum dose is 1 million cells per 300 g mouse injected in 200 to 300 µl across several seconds, in media containing 3% fetal bovine serum. Human AMSCs are known to cause pulmonary embolism due to aggregation in circulation, and similar phenomenon has been found in mice injected with 3 million cells in 200-300 µl of injection medium.

The cell survival after being stored in injection medium for 45 min was analyzed, since it is anticipated that a human application will require some time for infusion due to preparation etc. during this time, a mean survival was found (by trypan blue dye exclusion testing) as shown in the Table 2.

TABLE 2

| | In-Vivo model Injection medium | | | |
|---|---|---|---|---|
| | *FBS | | **SR | |
| PBS+ | 1% | 3% | 1% | 3% |
| Survival rate after 45 min. | %88 | %91 | %80 | %66 |

Route of injection
Cell numbers

100k → 300k → 1M → ✗

*FBS is fetal bovine serum;
**SR is serum replacement

It was found that lethal irradiation led to vascular leakiness, and therefore a 24 hour waiting period was instituted prior to cell injection in order to avoid vascular leakage. This allowed an injection of 10 fold more cells.

Figure 7:
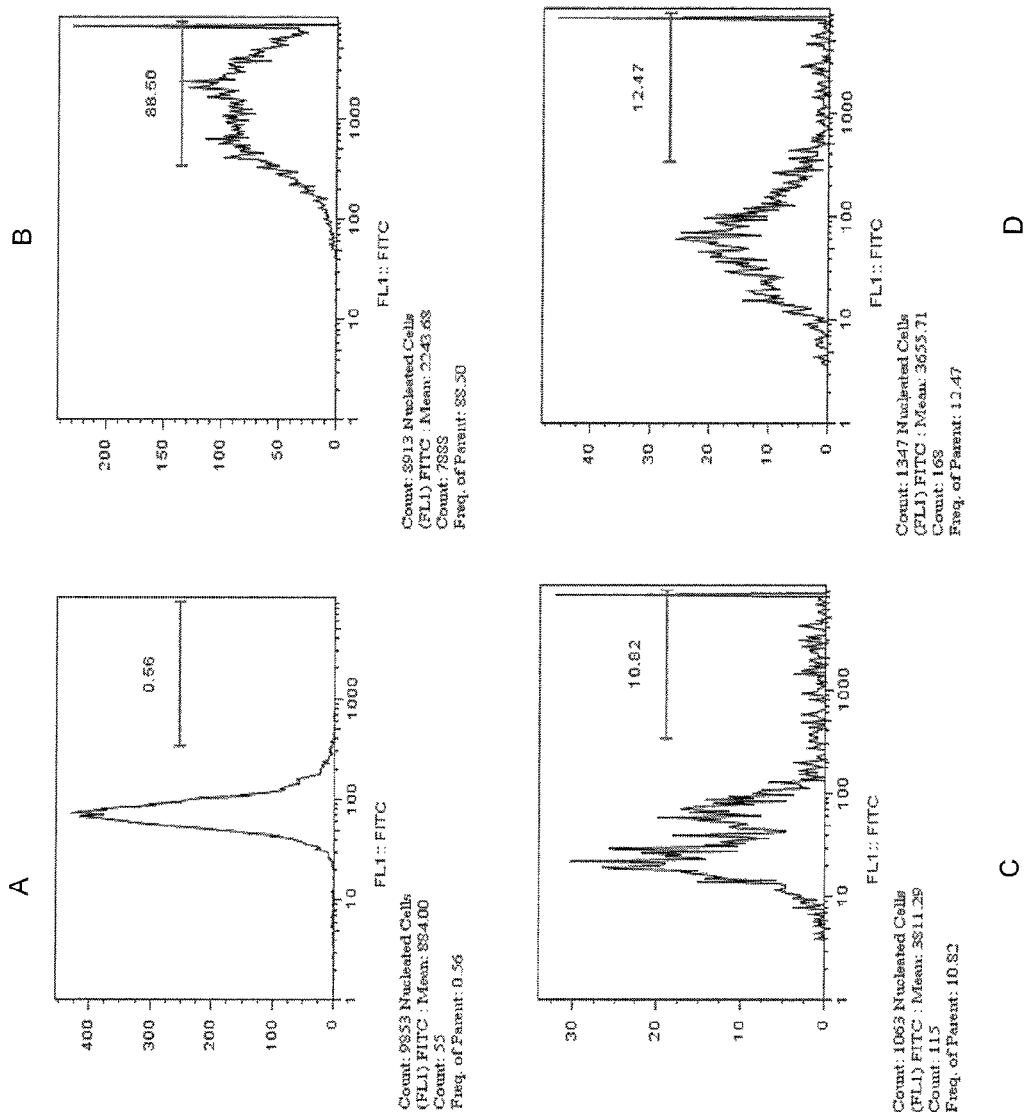
FIGS. 7A-7E is FACS analysis of cells stained for expression of HLA-G.

One or two weeks after injection with hAMCS, approximately 1/3 of the total blood volume (750 µl) was collected from each mouse and sorted based on binding by an anti-human HLA class I antibody (e.g., being FITC+). The analysis is shown in FIGS. 7A-7E and Table 3 below. For flow cytometric analysis of human HLA class I expression, a human choriocarcinoma cell line known to express HLA-G, Jeg-3, was used as a positive control and murine 3T3 cells were used as a negative control. Shown in FIGS. 7A and 7B, Jeg-3 cells are approximately 88.5% positive for anti-human HLA class I antibody. Only 0.5% of 3T3 cells were positive. These data were used to set the gating criteria to exclude anything that was not beyond this background non-specific binding. As shown in FIGS. 7C and 7D, one or two weeks after injection of $1\times10^5$ hAMSCs, 10.82% and 12.47% of collected blood cells were positive for human HLA class 1, respectively. Shown in FIG. 7E, after lethal irradiation and injection with $1\times10^5$ hAMSC, 80.86% of peripheral blood cells collected were positive for human HLA class I antigen. A summary of the results is shown in Table 3.

TABLE 3

| # Donor cells Transplanted | Recipient | Follow-up Period | # of nucleated cells in 10⁴ events | # of HLA I (+) cells in nucleated cells | Frequency of HLA I (+) cells |
|---|---|---|---|---|---|
| 3 × 10⁶ Mouse NIH-3T3 | N/A | n/a | 9853 | 55 | 0.56% |
| 3 × 10⁶ Human Jeg-3 | N/AI | n/a | 8913 | 7888 | 88.5% |
| 1 × 10⁵ hAMSCs | Immunocompetent Mice | 1 week | 1063 | 115 | 10.82% |
| 1 × 10⁵ hAMSCs | Immunocompetent Mice | 2 weeks | 1347 | 168 | 12.47% |
| 1 × 10⁵ hAMSCs | Lethally Irradiated Mice | 1 week | 162 | 131 | 80.86% |
| 1 × 10⁶ hAMSCs | Immunocompetent Mice | 2 weeks | 500k* | 41k | 8% |

As shown in FIG. 8, by RT-PCR, there is continued expression of HLA-G by the mesenchymal stem cells. FIG. 8 shows the RT-PCR results of Jeg-3 and AMSCs using HLA-G specific primer. FIGS. 9 and 10 demonstrates a lack of HLA-G transcripts by RT-PCR by HLA-G⁻ MSC.

Figure 11:
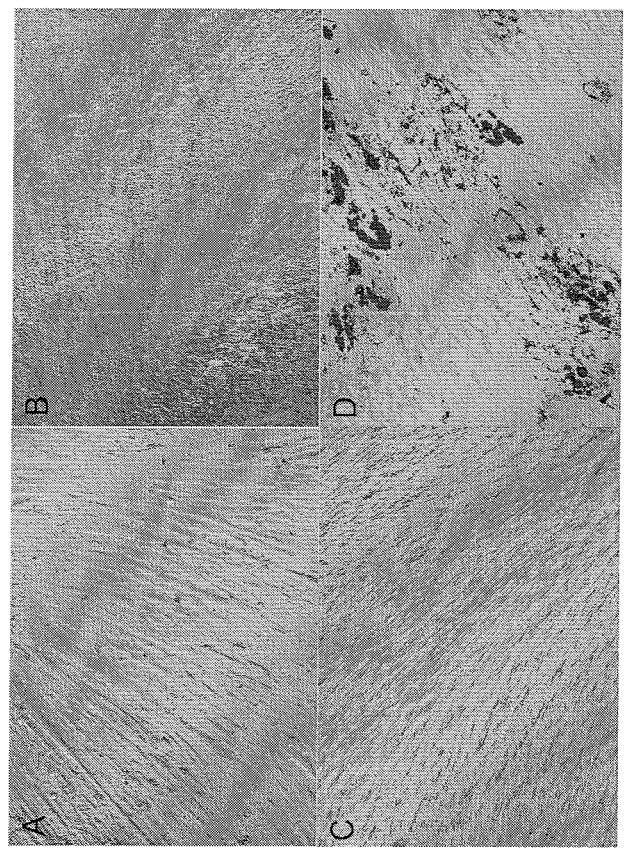
FIGS. 11A-11B are hAMSCs stained with Fast Blue RR to detect the activity of alkaline phosphatase (A, B) or oil red O to detect oil droplet (C, D) after culture in DMEM (A, C) osteogenic medium (B) or adipogenic medium (D).

Mesenchymal Multipotency Experiments: Human adipose mesenchymal stem cells multipotentiality was determined by culturing MSCs in DMEM, osteogenic medium, or adipogenic medium for 7 days according to well-known methods. Differentiation was evaluated by staining Fast Blue RR to detect the alkaline phosphatase of cells cultured in osteogenic medium or by staining with Nile Red Oil solution (Sigma) to detect oil droplets of cells cultured in adipogenic medium. The results are shown in FIG. 11.

What is claimed is:

1. An isolated composition of human cells comprising an enriched population of human adult adipose tissue derived mesenchymal stem cells or bone marrow derived mesenchymal stem cells, wherein at least 90% of said mesenchymal stem cells express cell surface marker HLA-G, HLA-E, or both HLA-G and HLA-E, wherein said enriched population of mesenchymal stem cells, upon initial isolation from adipose tissue or bone-marrow tissue, maintain cell surface expression of HLA-G, HLA-E, or both HLA-G and HLA-E, after at least two passages in non-differentiating in vitro culture conditions.

2. The composition of claim 1, wherein said mesenchymal stem cells do not express cell surface HLA-E after five passages in non-differentiating in vitro culture conditions.

3. The composition according to claim 1, wherein the human mesenchymal stem cells further express CD200.

4. The composition according to claim 1, wherein the human mesenchymal stem cells further express INDO (indoleamine-pyrrole 2,3 dioxygenase).

5. The composition according to claim 1, wherein the human mesenchymal stem cells further comprise an exogenous nucleic acid.

6. The composition according to claim 5, wherein said exogenous nucleic acid comprises a coding sequence for a polypeptide sequence of interest, operably connected to a promoter sequence active in said human mesenchymal stem cells.

7. The composition according to claim 5, wherein said exogenous nucleic acid comprises a sequence encoding HLA-G or HLA-E.

* * * * *

UNITED STATES PATENT AND TRADEMARK OFFICE
CERTIFICATE OF CORRECTION

PATENT NO. : 8,647,871 B2  
APPLICATION NO. : 12/532512  
DATED : February 11, 2014  
INVENTOR(S) : Basil M. Hantash It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this

Twenty-ninth Day of September, 2015

Michelle K. Lee
*Director of the United States Patent and Trademark Office*